United States Patent
Yoon et al.

(10) Patent No.: US 8,658,403 B2
(45) Date of Patent: Feb. 25, 2014

(54) METHOD FOR PRODUCING POLYHYDROXYALKANOIC ACID

(75) Inventors: Sung Chul Yoon, Jinju-si (KR); Ju Xu, Jinju-si (KR); Mun Hwan Choi, Jinju-si (KR)

(73) Assignee: Industry-Academic Cooperation Foundation Gyeongsang National University, Jinju-Si, Gyeongsangnam-Do (KR)

( * ) Notice: Subject to any disclaimer, the term of this patent is extended or adjusted under 35 U.S.C. 154(b) by 365 days.

(21) Appl. No.: 12/766,374

(22) Filed: Apr. 23, 2010

(65) Prior Publication Data

US 2011/0020886 A1 Jan. 27, 2011

(30) Foreign Application Priority Data

Jul. 27, 2009 (KR) .................... 10-2009-0068387

(51) Int. Cl.
*C12P 7/42* (2006.01)

(52) U.S. Cl.
USPC ........................................ 435/146

(58) Field of Classification Search
USPC ........................................ 435/146
See application file for complete search history.

(56) References Cited

PUBLICATIONS

Lee et al. [Journal of Microbiology and Biotechnology (2004), 14(6), 1256-1266].*
Rho et al. [Journal of microbiology and biotechnology, (Dec. 2007) vol. 17, No. 12, pp. 2018-2026].*
"Recent Trends in Bioconvergence Technology", The Korean Society for Microbiology and Biotechnology, Jun. 25-26, 2009, Daejeon Convention Center, Korea.

* cited by examiner

*Primary Examiner* — Tekchand Saidha
(74) *Attorney, Agent, or Firm* — Kile Park Reed & Houtteman PLLC

(57) ABSTRACT

Provided is a method for producing a polyhydroxyalkanoic acid (PHA). More particularly, a method of preparing PHA containing a high content of long-chain aromatic monomer-units by growing a phaZ mutant of a *Pseudomonas* strain in a medium containing a sugar, a substituted fatty acid, and a salicylic acid.

10 Claims, 10 Drawing Sheets

SEQUENCE LISTING

<160> NUMBER OF SEQ ID NOS: 5

<210> SEQ ID NO 1
<211> LENGTH: 28
<212> TYPE: DNA
<213> ORGANISM: Artificial Sequence
<220> FEATURE:
<223> OTHER INFORMATION: primer

<400> SEQUENCE: 1
cgcgaattct tccgtaccgt caacctgg          28

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2

```
gctctagagg atcttgtgca gccagtga                                      28

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
ggtcatagct gtttcctgtc ag                                            22

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4
atctcgagtt acagggcttc gtgcatg                                       27

<210> SEQ ID NO 5
<211> LENGTH: 28
<212> TYPE: DNA
<213> ORGANISM: Artificial Sequence
<220> FEATURE:
<223> OTHER INFORMATION: primer

<400> SEQUENCE: 5
cctctagatc accatagacg ttgttgcg                                      28
```

METHOD FOR PRODUCING POLYHYDROXYALKANOIC ACID

CROSS-REFERENCE TO RELATED APPLICATION

This application claims the benefit of Korean Patent Application No. 2009-0068387, filed Jul. 27, 2009, the disclosure of which is hereby incorporated herein by reference in its entirety.

BACKGROUND OF THE INVENTION

1. Field of the Invention

The present invention relates to a method for producing a polyhydroxyalkanoic acid (PHA), and more particularly, to a method for producing a polyhydroxyalkanoic acid containing a high content of long-chain aromatic monomer-units by growing a phaZ mutant of a *Pseudomonas* strain in a medium containing a sugar, a substituted fatty acid, and a salicylic acid.

2. Description of the Related Art

Polyhydroxyalkanoic acids (PHAs) are polyesters accumulated as an intracellular carbon and energy storage material in various microorganisms under unbalanced growth condition of limiting nutritional elements such as phosphorous, nitrogen, magnesium, and oxygen in the presence of excess carbon source. PHAs have attracted much attention as promising substitutes for chemically synthesized polymers due to their similar mechanical properties to petroleum-derived plastics and complete biodegradability.

PHAs are accumulated in a wide range of microorganisms in the form of granular inclusion bodies. The PHAs that microorganisms produce are divided into two classes, short-chain-length (SCL-) PHAs ($C_4$ and $C_5$) and medium-chain-length (MCL-) PHAs ($C_6$-$C_{14}$). MCL-PHAs have attracted attention because of the possible incorporation of many functional groups, such as phenyls, phenoxy groups, alkenes, etc., into their side chains, thereby resulting in the improved properties such as the increased transparency. For example, the MCL-PHA containing a monomer derived from MCL fatty acids having an aromatic substituent at the co-position may be used as a starting intermediate in pharmacology and in various fields.

MCL-PHA producing *Pseudomonas* spp. are typical bacteria that can produce aromatic polyesters from phenyl group carboxylic acids. However, some precursors containing a phenyl group or modified phenyl group, such as 5-phenylvalerate, (5PV), 5-(4-tolyl)-valerate, etc., are not readily utilizable by bacteria when they are fed as the sole carbon source. In order to increase the utilization capability of recalcitrant carbon compounds, the cometabolism method has been suggested. Most studies have is employed the cometabolism method in which a good polymer-producing substrate (such as either octanoic acid or nonanoic acid) has usually been used as a cosubstrate. Accordingly, since the resulting polymer obtained by the cometabolism method is a mixture of an aromatic homopolymer, an aromatic/aliphatic copolymer, and an aliphatic polymer, the isolation and purification of pure aromatic homopolyester from the recovered mixed polymer sample requires a tedious fractionation procedure using repetitive solution precipitation steps.

Therefore, it has been necessary to develop a technology for producing pure aromatic polyester in quantity. It has been seen that some carboxylic acids having low carbon number ($C_2$-$C_5$), fructose, and glucose in *Pseudomonas putida* BM01 do not induce PHA production but support the growth of a large amount of cells. The use of carbon sources in cometabolism with w-phenylalkanoic acids or 11-phenoyundecanoic acids (11-POU) resulted in a high production of pure aromatic polyesters free from aliphatic monomer-units in *Pseudomonas putida* BM01.

Inhibitors for PHA synthesis may be used to carry intermediates in a specific metabolic pathway to the PHA synthesis pathway. Acrylic acid is known as a β-oxidation inhibitor for bacteria, and when *Ralstonia eutropha*, which is a typical bacterium that accumulates SCL-PHA, was grown using octanoic acid as a carbon source, the acrylic acid was successfully used to introduce the MCL monomer as a comonomer to the PHA. It is known that 2-bromooctanoic acid (2-BrOA) does not affect cell growth on sugars but inhibits only MCL-PHA accumulation in *Pseudomonas* spp. Therefore, 2-BrOA effectively inhibits the production of PHA composed of (R)-3-hydroxyacyl monomers, induced by ((R)-3-hydroxyacyl)-ACP 4 CoA transferase (PhaG) from the coadded, unrelated carbon source such as sucrose, it can be effectively used in the preparation of PHA which is functionally designed from carboxylic acid having a functional group in *Pseudomonas* spp.

Recently, another inhibitor for the production of MCL-PHA has been reported. When *Pseudomonas aeruginosa* BM114 capable of accumulating both SCL-PHA and MCL-PHA was grown in a medium-chain carboxylic acid (e.g., C8, C9 and $C_{10}$ carboxylic acids), while the treatment of acrylic acid just inhibited the production of SCL-PHA, the treatment of salicylic acid just inhibited the production of MCL-PHA.

The material properties of MCL-PHA depend on the length and uniformity of spacer side-chain with a functional pendent group. Thus, modulation of the distribution of side-chain monomer-units is expected to improve material properties.

Generally, the monomer distribution in MCL-PHA depends on the specificity of PHA synthase and the intracellular concentration of monomer precursors. When MCL fatty acids are used as carbon source, the monomer precursors are mostly supplied through enzyme(s) (e.g., enoyl-CoA hydratase (PhaJ) linking the β-oxidative pathway and the PHA synthesis pathway. In the previous study of the inventors of the present invention, under a synthetic strategy that combined the β-oxidation inhibition by salicylic acid and cometabolism of 11-POU and fructose, *Pseudomonas fluorescens* BM07 was able to shift the distribution of aromatic medium-chain-length monomer-units in the PHA to longer units.

Thus, salicylic acid could be an efficient mediator in producing longer monomer precursors like 3-hydroxy-9-phenoxynonanoate (9POHN), twice as much as in a simple cosubstrate method. Since the cell growth is insignificant in a medium containing only 11-POU as a single carbon source in the presence of salicylic acid, the significant increase by salicylic acid was possible only by the cosubstrate metabolism using fructose and 11-POU.

Intracellular PHA depolymerase PhaZ is responsible for the degradation or intercellular PHA granules to supply the hydrolyzed monomer energy and other ingredients in cells. Deletion of phaZ in *Pseudomonas putida* KT2442 has been known to increase the accumulation of PHA in the cell when the mutant cell was grown on octanoate. Meanwhile, disruption of phaZ gene was expected to affect intracellular levels and half-lives of β-oxidation intermediates, eventually affecting the rate of incorporation of 3-hydroxy-monomer-units into PHA from the coadded functional fatty acids (e.g., 11-POU). In the present invention, the phaZ gene in *P. fluorescens* BM07 was disrupted using an insertional mutagenesis technique and the effect of salicylic acid on the shifting of aromatic monomer-unit distribution as well as the production of the aromatic PHA in the mutant was investigated.

The inventors of the present invention have found that the salicylic acid (1 mM) treatment significantly increased the level of longer aromatic monomer-units and the yield of conversion of 11-POU to PHA in BM07-ΔphaZ mutant. In addition, the phaZ gene was over-expressed in the wild-type strain to assess how PhaZ affects the comonomer composition of aromatic PHA. Enhancement of the conversion yield by salicylic acid was also observed for other types of aromatic carboxylic acids such as 5-phenylvalerate (5PV) and 6-phenylcaproate (6PC).

SUMMARY OF THE INVENTION

The present invention is directed to a method for producing a high-purity aromatic polyhydroxyalkanoic acid containing a high content of longer side-chain aromatic monomer-units than in a wild-type strain, using a phaZ mutant of a *Pseudomonas* strain.

In one aspect, the present invention provides a method for producing a polyhydroxyalkanoic acid, the method including growing a *Pseudomonas* strain in a medium containing a sugar, a substituted fatty acid, and a salicylic acid to yield a high-purity aromatic polyhydroxyalkanoic acid containing a high content of long-chain aromatic monomer-units.

In another aspect, the present invention provides a method producing a polyhydroxyalkanoic acid, the method including: (i) deleting a gene of polyhydroxyalkanoic acid depolymerase from a *Pseudomonas* strain and preparing a mutant of the *Pseudomonas* strain; and (ii) yielding a high-purity aromatic polyhydroxyalkanoic acid containing a high content of long-chain aromatic monomer-units from the mutant of the *Pseudomonas* strain.

In still another aspect, the present invention provides a method for producing a polyhydroxyalkanoic acid, the method including: (i) growing a *Pseudomonas* strain in a medium containing a sugar, a substituted fatty acid, and a salicylic acid; (ii) deleting a gene of polyhydroxyalkanoic acid depolymerase from the *Pseudomonas* strain and preparing a mutant of the *Pseudomonas* strain; and (iii) yielding a high-purity aromatic polyhydroxyalkanoic acid containing a high content of long-chain aromatic monomer-units from the mutant of the *Pseudomonas* strain.

In yet another aspect, the present invention provides a mutant produced by deleting a gene of polyhydroxyalkanoic acid depolymerase from a *Pseudomonas* strain.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 3A to 3C show the NMR analysis of the three samples (samples 1, 2, and 4) with different compositional ratios of monomer-units calculated in Table 2, in which FIG. 3A shows 500 MHz H-NMR spectra, FIG. 3B shows 125 MHz $^{13}$C-NMR spectra (shown for phenoxy-CH2-methylene carbon region only), and FIG. 3C shows 2D hetero-COSY NMR spectra (the cross-peaks are shown for phenoxy-CH2-methylene region only). For all spectra in FIGS. 3A to 3C, the upper spectrum is for sample 1, the middle spectrum is for sample 2, and the bottom spectrum is for sample 4.

DETAILED DESCRIPTION OF THE INVENTION

Figure 1:
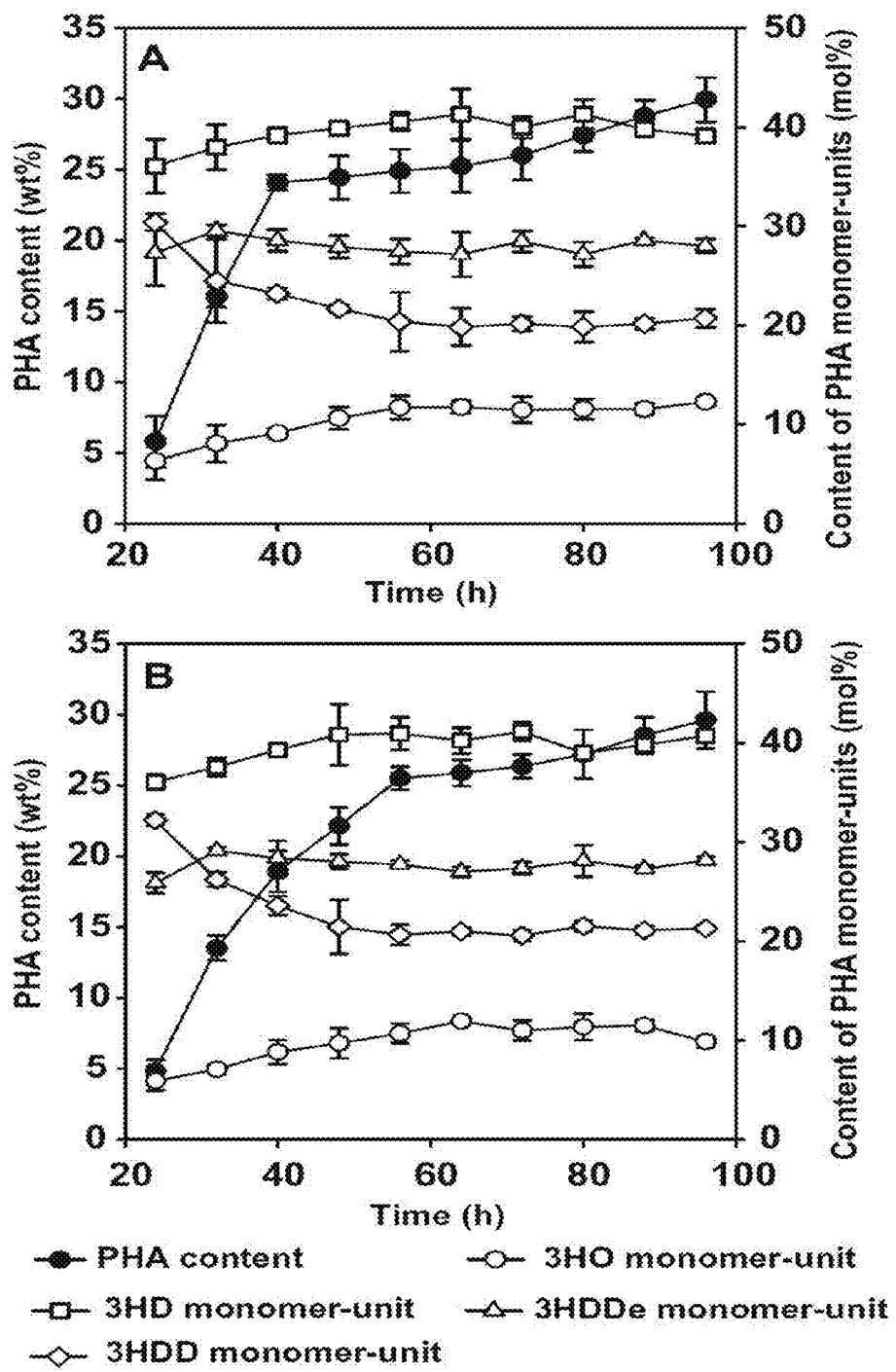
FIG. 1 shows the comparison of time-course profiles for PHA accumulation in (A) BM07 wild-type, (B) BM07-ΔphaZ mutant, (C) BM07 (pBBR-phaZ), and (D) BM07-ΔphaZ (pBBR-phaZ) grown on 70 mM fructose in M1 medium at 30° C., and (E) shows the comparison of time dependent PHA content between BM07 wild-type and BM07-ΔphaZ mutant grown on 40 mM octanoic acid in M1 medium at 30° C., wherein all values are averages in duplicate experiments.
Figure 1:
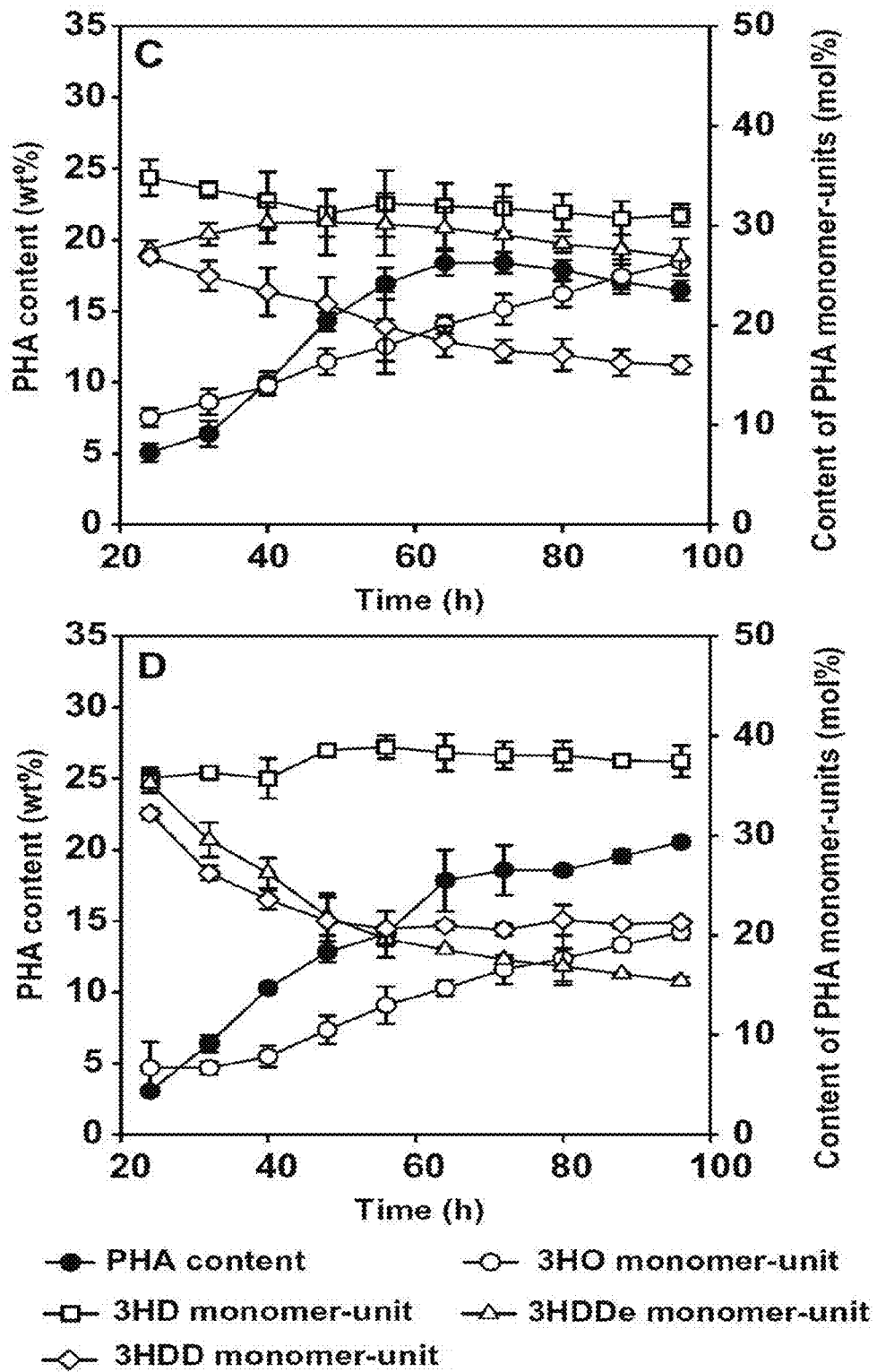
Figure 1:
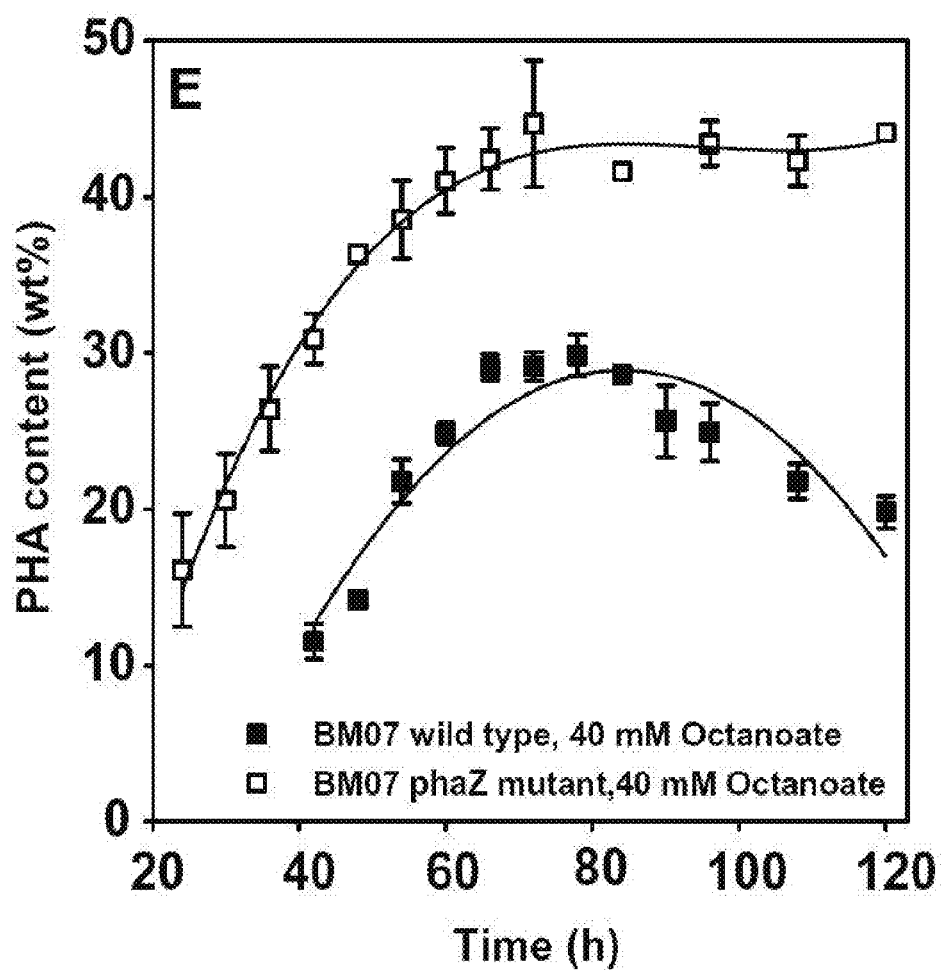

Hereinafter, exemplary embodiments of the present invention will be described in detail. However, the present invention is not limited to the exemplary embodiments disclosed below, but can be implemented in various types. Therefore, the present exemplary embodiments are provided for complete disclosure of the present invention and to fully inform the scope of the present invention to those ordinarily skilled in the art.

An aspect of the present invention provides a method for producing a polyhydroxyalkanoic acid by growing a *Pseudomonas* strain in a medium containing a sugar, a substituted fatty acid, and a salicylic acid to yield a high-purity aromatic polyhydroxyalkanoic acid containing a high content of long-chain aromatic monomer-units.

The *Pseudomonas* strain may be *Pseudomonas fluorescens*, and preferably, *Pseudomonas fluorescens* BM07 (Accession no.: KCTC 10005BP).

The sugar may be one capable of being used as a carbon source for growth of the *Pseudomonas* strain. Examples of the sugar include fructose, glucose, galactose, mannose, etc., and preferably fructose. The sugar content in the medium may be 50 to 70 mM, and preferably 50 mM.

The substituted fatty acid may be, but not limited to, a substituted aromatic carboxylic acid, and preferably a carboxylic acid substituted with a phenyl, substituted phenyl, or phenoxy group. The content of the substituted fatty acid in the medium may be, but not limited to, 3 to 10 mM.

The content of the salicylic acid in the medium may be 0.1 to 2 mM, and preferably 1 mM.

The medium may be one suitable for the growth of the *Pseudomonas* strain, and preferably M1 mineral salts medium (1.06 g $(NH_4)_2SO_4$, 2.3 g $KH_2PO_4$, 7.3 g $Na_2HPO_4.12H_2O$, 0.25 g $MgSO_4.7H_2O$, 0.3 g $NaHCO_3$, 0.1 g $CaCl_2.2H_2O$, 0.03 g ferric ammonium citrate, and 2 ml microelement solution). The microelement solution is produced by adding 0.556 g $FeSO_4.7H_2O$, 0396 g $MnCl_2.4H_2O$, 0.034 g $CuCl_2.2H_2O$, 0.06 g $H_3BO_3$, 0.006 g $NaMoO_4.2H_2O$, 0.562 g $CoSO_4.7H_2O$, 0.058 g $ZnSO_4.7H_2O$, and 0.004 g $NiCl_2.6H_2O$ to 200 ml of 0.5N hydrochloric acid.

The stain may be grown to reach maximum growth at 10 to 30° C., and preferably 30° C.

The aromatic monomer unit may be one selected from the group consisting of 3-hydroxy-5-phenoxyvalerate (5POHV), 3-hydroxy-7-phenoxyheptanoate (7POHH), 3-hydroxy-9-phenoxynonanoate (9POHN), and 3-hydroxy-11-phenoxyundecanoate (11POHUN).

Another aspect of the present invention provides a method for producing a polyhydroxyalkanoic acid, the method including: (i) deleting a gene of polyhydroxyalkanoic acid depolymerase from a *Pseudomonas* strain and preparing a mutant of the *Pseudomonas* strain; and (ii) yielding a high-purity aromatic polyhydroxyalkanoic acid containing a high content of long-chain aromatic monomer-units from the mutant of the *Pseudomonas* strain.

The *Pseudomonas* strain may be *Pseudomonas fluorescens*, and preferably *Pseudomonas fluorescens* BM07 (Accession no.: KCTC 10005BP).

The gene of the polyhydroxyalkanoic acid depolymerase may be phaZ (GenBank accession no: FJ472565).

The aromatic monomer-units may be one selected from the group consisting of 3-hydroxy-5-phenoxyvalerate (5POHV), 3-hydroxy-7-phenoxyheptanoate (7POHH), 3-hydroxy-9-phenoxynonanoate (9POHN), and 3-hydroxy-11-phenoxyundecanoate (11POHUN).

Still another aspect of the present invention provides a method for producing a polyhydroxyalkanoic acid, the method including: (i) growing a *Pseudomonas* strain in a medium containing a sugar, a substituted fatty acid, and a salicylic acid; (ii) deleting a gene of polyhydroxyalkanoic acid depolymerase from the *Pseudomonas* strain and preparing a mutant of the *Pseudomonas* strain; and (iii) yielding a high-purity aromatic polyhydroxyalkanoic acid containing a high content of long-chain aromatic monomer-units from the mutant of the *Pseudomonas* strain.

The *Pseudomonas* strain in Step (i) may be *Pseudomonas fluorescens*, and preferably *Pseudomonas fluorescens* BM07 (Accession no.: KCTC 10005BP).

The sugar in Step (i) may be one capable of being used for the growth of the *Pseudomonas* strain. Examples of the sugar may include fructose, glucose, galactose, mannose, etc., and preferably fructose. The sugar content in the medium may be 50 to 70 mM, and preferably 50 mM.

The substituted fatty acid in Step (i) may be, but not limited to, a substituted aromatic carboxylic acid, and preferably a carboxylic acid substituted with a phenyl, substituted phenyl, or phenoxy group. The content of the substituted fatty acid in the medium may be, but not limited to, 3 to 10 mM.

The content of the salicylic acid in Step (i) may be 0.1 to 2 mM, and preferably 1 mM.

The medium in Step (i) may be one suitable for the growth of the *Pseudomonas* strain, and preferably M1 mineral salts medium (1.06 g $(NH_4)_2SO_4$, 2.3 g $KH_2PO_4$, 7.3 g $Na_2HPO_4.12H_2O$, 0.25 g $MgSO_4.7H_2O$, 0.3 g $NaHCO_3$, 0.1 g $CaCl_2.2H_2O$, 0.03 g ferric ammonium citrate and 2 ml microelement solution). The microelement solution is produced by adding 0.556 g $FeSO_4.7H_2O$, 0.396 g $MnCl_2.4H_2O$, 0.034 g $CuCl_2.2H_2O$, 0.06 g $H_3BO_3$, 0.006 g $NaMoO_4.2H_2O$, 0.562 g $CoSO_4.7H_2O$, 0.058 g $ZnSO_4.7H_2O$, and 0.004 g $NiCl_2.6H_2O$ to 200 ml of 0.5N hydrochloric acid.

The stain may be grown to reach maximum growth at 10 to 30° C., and preferably 30° C.

Prior to Step (i), seed-culturing the *Pseudomonas* strain may be further included. Preferably, the seed culture of the *Pseudomonas* strain may be performed by culturing cells in nutrient-rich (NR) medium (containing 1% yeast extract, 1.5% nutrient broth, and 0.2% ammonium sulfate) at 30° C. and 175 rpm for 12 hours.

The gene of the polyhydroxyalkanoic acid depolymerase in Step (ii) may be phaZ (GenBank accession no: FJ472565).

The aromatic monomer unit in Step (iii) may one selected from the group consisting of 3-hydroxy-5-phenoxyvalerate (5POHV), 3-hydroxy-7-phenoxyheptanoate (7POHH), 3-hydroxy-9-phenoxynonanoate (9POHN), and 3-hydroxy-11-phenoxyundecanoate (11 POHUN).

Moreover, the present invention provides a mutant produced by deleting a gene of polyhydroxyalkanoic acid depolymerase from a *Pseudomonas* strain. The *Pseudomonas* strain may be *Pseudomonas fluorescens*, and preferably *Pseudomonas fluorescens* BM07 (Accession no.: KCTC 10005BP).

The gene of the polyhydroxyalkanoic acid depolymerase may be phaZ (GenBank accession no: FJ472565).

Hereinafter, examples according to the present invention will be described with reference to the accompanying drawings. The following examples are to explain the present invention, which is not provided to limit the present invention.

EXAMPLES

Bacterial Strains and Culture Media for PHA Production

*Pseudomonas fluorescens* (P fluorescens) BM07 isolated in a lab and three BM07 mutant strains as shown in Table 1 were used for comparison. Nutrient rich (NR) medium containing 1% yeast extract, 1.5% nutrient broth, and 0.2% ammonium sulfate was used in the seed-culture, maintenance and storage of the wild-type strain. In the seed culture of the mutants, a colony was inoculated into Luria Bertani (LB) medium and cultivated at 30° C., 175 rpm for 12 hours. The M1 mineral salts medium (1.06 g $(NH_4)_2SO_4$, 2.3 g $KH_2PO_4$, 7.3 g $Na_2HPO_4.12H_2O$, 0.25 g $MgSO_4.7H_2O$, 0.3 g $NaHCO_3$, 0.1 g $CaCl_2.2H_2O$, 0.03 g ferric ammonium citrate and 2 ml microelement solution) was used as PHA synthesis medium. The microelement solution is produced by adding 0.556 g $FeSO_4.7H_2O$, 0.396 g $MnCl_2.4H_2O$, 0.034 g $CuCl_2.2H_2O$, 0.06 g $H_3BO_3$, 0.006 g $NaMoO_4.2H_2O$, 0.562 g $CoSO_4.7H_2O$, 0.058 g $ZnSO_4.7H_2O$, and 0.004 g $NiCl_2.6H_2O$ to 200 ml of 0.5N hydrochloric acid.

TABLE 1

Strains, plasmids and oligonucleotides used in the examples of the present invention

| Strains/Plasmids | Relevant Characteristics | Sources or References |
|---|---|---|
| Strains | | |
| E. coli S17-1 | recA harboring the tra genes of plasmid RP4 in the chromosome, proA, thi-1 | Simon et al. (1983) |
| P. fluorescens BM07 | Wild-type, isolated from activated sludge, medium-chain-length polyhydroxyalkanoates-producing strain | Lee et al. 2001 |
| BM07-ΔphaZ | Derivative of BM07, phaZ, phaZ-lacZ | this study |
| BM07 (pBBR-phaZ) | BM07 derivative containing pBBR-phaZ | this study |
| BM07-ΔphaZ (pBBR-phaZ) | BM07-ΔphaZ mutant derivative containing pBBR-phaZ | this study |
| Plasmids | | |
| pVIK112 | R6 K, promoterless lacZ, $Km^R$ | Kalogeraki and Winans (1997) |
| pXJZ | phaZ internal fragment in pVIK112 | this study |
| pBBR1MCS2 | $Cm^R$ broad host vector | Kovach et al. (1995) |
| pBBR-phaZ | pBBR1MCS2 derivative containing phaZ gene from P. fluorescens BM07 | |
| Oligonucleotides | | |
| 07ZF-F | 5'-CGCGAATTCTTCCGTACCGTCAACCTGG-3' (SEQ ID NO. 1) | |
| 07Z-R | 5'-GCTCTAGAGGATCTTGTGCAGCCAGTGA-3' (SEQ ID NO. 2) | |
| pVIK-R | 5'-GGTCATAGCTGTTTCCTGTCAG-3' (SEQ ID NO. 3) | |
| 07phaZ-F | 5'-ATCTCGAGTTACAGGGCTTCGTGCATG-3' (SEQ ID NO. 4) | |
| 07phaZ-R | 5'-CCTCTAGATC ACCATAGACG TTGTTGCG-3' (SEQ ID NO. 5) | |

In the main cultures, 500 μl of the culture grown in NR or LB medium was transferred to 50 ml M1 mineral-salts medium containing 50 mM fructose, 5 mM 11-POU, 0 or 1 mM salicylic acid and 1.0 g/L ammonium sulfate in a 250 mL flask and cultivated at 30° C. Salicylic acid was dissolved by adding sodium hydroxide and the pH of the solution was adjusted to 7.2 before adding to medium. Cell growth was determined by measuring dry cell weight (DCW). The remaining fructose was measured using DNS method and the remaining 11-POU or other carboxylic acids were determined by gas chromatography. The cells were isolated by centrifuging (10,000×g, 10 min), the cell suspension was washed with methanol and dried under vacuum at room temperature for 48 hours. The remaining $NH_4^+$ was measured using Nessler's reagent. In the time-course profiling experiments, a set of culture flasks equal to the planned sampling times (every 4 or 6 h) was prepared and cultivated under the same culture condition. One of the flasks was withdrawn every scheduled time and the medium (50 ml) was centrifuged and analyzed.

Preparation of Mutant of phaZ Gene (BM07-ΔphaZ), Complement (BM07-ΔphaZ (pBBR-phaZ)) and Over-Expressed Strain (BM07 (pBBR-phaZ)) from P. fluorescens BM07

Bacterial stains, plasmids and oligonucleotides used in the examples are listed in Table 1. Escherichia coli strains were grown with shaking (180 rpm) at 37° C. in LB medium. When required, an appropriate amount of antibiotics (e.g., 20 μg/ml kanamycin, 100 μg/ml ampicillin, or 34 μg/ml chloramphenicol) were added to the medium. Plasmid isolation, gel electrophoresis, transformation, PCR and cloning for vector construction were performed by standard procedures.

Insertional mutagenesis was used to generate a mutant by single homologous recombination. The internal region of P. fluorescens BM07 phaZ (GenBank accession number: FJ472656) was amplified by the 07Z-F/07Z-R primer pair to yield a 309-bp fragment. The amplified 309-bp fragment was cloned into EcoR I and XbaI cloning sites of pVIK112 vector to generate pXJZ. The pXJZ plasmid was then introduced into E. coli S17-λpir by electroporation.

Conjugation was performed by filter mating with E. coli S17-1 λpir (pXJZ) and P. fluorescens BM07 as donor and recipient, respectively. The transconjugants were selected on LB agar medium containing X-gal, kanamycin and ampicillin after incubation at 30° C. for 24 hours. Polymerase chain reaction (PCR) with 07Z-F/pVIK-R primer pair was performed to confirm the transconjugants. The pVIK-R primer was designed based on the sequence information of the pVIK112 plasmid. PCR using the 07Z-F/pVIK-R primer pair resulted in the expected size of fragment only in the transconjugant. The intact phaZ gene of *P. fluorescens* BM07 was amplified by primers 07phaZ-F and 07phaZ-R by PCR using its genome as template. The PCR product was inserted into pBBR1MCS2 to prepare the plasmid pBBR-phaZ. The resulting plasmid was introduced into *P. fluorescens* BM07 wild-type and BM07-ΔphaZ mutant, thereby preparing BM07 (pBBR-phaZ) and BM07-ΔphaZ (pBBR-phaZ), respectively.

Quantitative Assay of PHA in Cells

The monomer composition of the PHA in cells was determined by analyzing the methyl esters, recovered from a sulfuric acid/methanol treatment of the cells, using a Hewlett-Packard HP5890 Series II gas chromatograph equipped with a HP-1 capillary column and a flame ionization detector. The gas chromatography (GC) run conditions were as follows: initial temperature of 80° C. for 2 min; heating rate of 8° C./min; final temperature of 250° C. for 6.75 min; carrier (He) flow rate of 3 ml/min; injector temperature of 230° C.; and detector temperature of 280° C. The standardization of each GC peak was made against the PHA of known structure characterized by quantitative NMR analyses Thermal Transition Analysis PHA was extracted with chloroform from cells using a Soxhlet apparatus for 8 hours. After evaporating chloroform, the resulting polymer was also dissolved in chloroform, reprecipitated in methanol, and dried in a vacuum drying oven for 24 hours. Thermal transitions of the purified PHA were measured using a differential scanning calorimeter (DSC) Q200 (TA Instruments) equipped with a data station system. The PHA samples for DSC characterization were prepared by aging 10 mg of the dried sample in situ in a DSC sample pan for at least 2 weeks or longer. The room temperature annealed PHA samples were heated at a rate of 10° C./min from −80 to 100° C.

NMR Analysis

125 MHz $^{13}$C- and 500 MHz $^{1}$H-NMR spectra were recorded on a Bruker AMX-500 spectrometer in the pulse-Fourier transform mode at 25° C. in a CDCl$_3$ solution of polyester (~30 mg/ml). Data collections for $^{13}$C NMR spectra were made with the program zgig30 in a gated decoupling mode with a 10μ pulse width, 30-s pulse repetition, 30000 Hz spectral width, 64 K data points, and 5000 accumulations. Tetramethylsilane was used as an internal chemical-shift standard. Two-dimensional homonuclear ($^{1}$H-$^{1}$H) and heteronuclear ($^{1}$H-$^{13}$C) correlation spectroscopy (COSY), HMBC, and DEPT spectra were also recorded at 25° C.

Gas Chromatography/Mass Spectrometry (GC/MS) Assay of 3-Hydroxyacid Methyl Esters The structural identification of 3-hydroxyacid methyl esters obtained after sulfuric acid/methanol hydrolysis was carried out using a GC/MS (Agilent 5975C) instrument equipped with HP-5MS 5% Phenyl Methyl Silox column. Helium was used as the carrier gas (1 ml/min).

Figure 2:
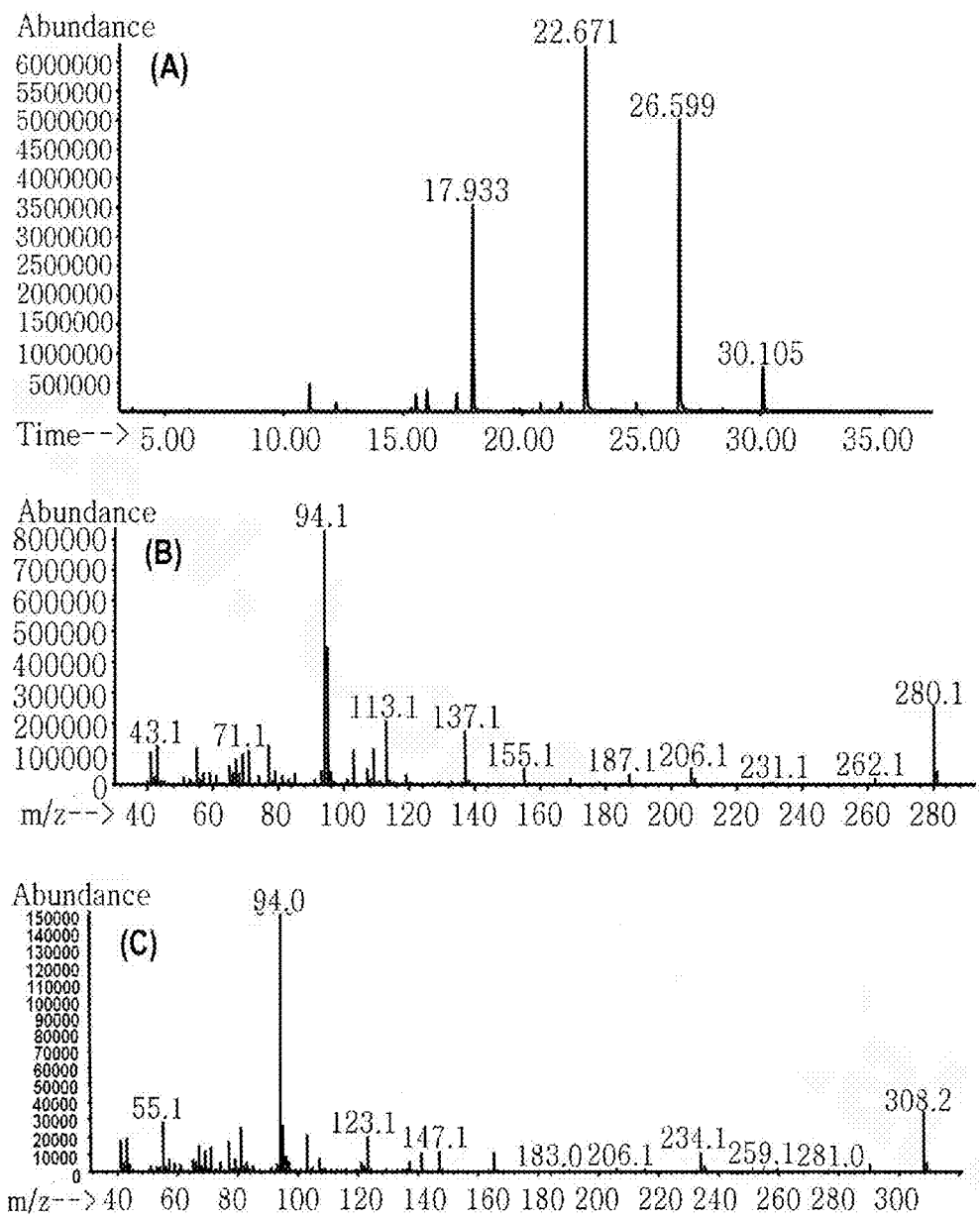
FIG. 2 shows the GC/MS analyses of methyl esters of 3-hydroxy monomer-units recovered by sulfuric acid/methanol hydrolysis of PHA produced in *Pseudomonas fluorescens* BM07-ΔphaZ grown on a mixture of 50 mM fructose, 8 mM 11-POU, and 1 mM salicylic acid, wherein (A) shows the isolation of methyl esters for four aromatic monomer-units in PHA by gas chromatography, (B) shows the cation m/z profile for the peak at 26.6 min in (A), and (C) shows the cation m/z profiles for the peak at 30.1 min peak in (A).

1 μl of the chloroform solution containing methyl esters was injected to the column. The temperature of the injector and detector was 270 and 280° C., respectively, and oven program of 120° C. for 5 minutes, 5° C./min to 250° C. for 5 min and then 10° C./min to 280° C. for 5 minutes was used. Since Agilent Instrument Data System had no mass spectral data for 11-POU derived 3-hydroxy methyl esters, peaks on the mass spectra were exactly assigned for its exact identification, which is shown in FIG. 2.

Increase in PHA Accumulation in BM07-ΔphaZ Mutants from Octanoate or Fructose

As shown in FIG. 1, maximum PHA accumulation was attained for the wild-type after the cultivation for 60 to 80 hours when the carbon source, fructose or octanoate was consumed. The disruption of phaZ in BM07 did not significantly shift the time to reach a steady-state for cell growth or PHA accumulation. The culture-time dependent profiles of octanoate or fructose consumption for the wild-type and phaZ mutant were quite similar.

The profiles of PHA accumulation and monomer compositional ratio of the wild-type and BM07-ΔphaZ mutant cells grown on 70 mM fructose were also comparable. Within 4 days of the first-step cultivation period, little PHA degradation was observed for the wild-type cells grown with fructose. However, 85% of the PHA in the wild-type cells grown with 70 mM fructose for 72 hours was degraded in a carbon source free medium containing 1 g/L ammonium sulfate after incubation of 48 hours, while no PHA degradation was observed in the BM07-ΔphaZ mutant cells under the same degradation condition as expected. Thus, the similar level of PHA accumulation for the two strains, wild-type and BM07-ΔphaZ mutant cells grown on fructose, may indicate that the degradation activity of the wild-type cells was too low in the fructose medium.

In contrast, according to FIG. 1, the BM07-ΔphaZ mutant grown on 40 mM octanoate accumulated PHA up to 44 wt % compared with the BM07 wild-type which produced only 17 wt % of its dry cell weight after 5 days of cultivation. Even at the maximum PHA accumulation, the octanoate-grown wild-type cells accumulated maximally to 29 wt %. The lowered maximum accumulation might support the notion that PHA biosynthesis is a dynamic process which intricately involves both polymerization and depolymerization activities even during active accumulation period when the nitrogen was consumed. Thus, similar to *P. putida* KT2442, the inactivation of phaZ in BM07 strain led to decreased degradation of PHA and thus to a concomitant increased accumulation of MCL-PHA. Contrarily, in *Pseudomonas resinovorans*, the mutation of phaZ was reported to have little effect on PHA accumulation. The cultivation of the BM07-ΔphaZ mutant accumulated a smaller amount (34 wt %) of PHA on 70 mM fructose than 40 mM octanoate. In the wild-type strain, the level (~27 wt %) of the PHA accumulated in the fructose medium was less decreased than that of the PHA accumulated in the octanoate medium.

To understand the probable role of PhaZ in PHA accumulation, the phaZ gene of BM07 was over-expressed and its culture-time dependent profile of monomer composition was investigated for the cells grown with 70 mM fructose. Compared to the wild-type, the phaZ gene over-expressed strain incorporated the shorter side-chain monomer-unit 3-hydroxyoctanoate (3HO) into PHA more increasingly with time than the wild-type. A less amount of 3-hydroxydecanoate (3HD) (~31 mol %) and 3-hydroxydodecanoate (3HDD) (~16 mol %) was incorporated in the overexpressed strain than the wild-type (~40 mol % and ~21 mol %, respectively). Thus, the overexpression of phaZ gene resulted in the production of PHA enriched with shorter monomer-units as well as the decreased production of PHA.

To exclude the possibility that the phenotypes observed in BM07-ΔphaZ mutant were caused by a polar effect (by different genes such as phaC1 or phaC2), a complement (BM07-ΔphaZ (pBBr-phaZ)) complementing the plasmid (pBBrphaZ) to which the phaZ gene was introduced into the BM07-ΔphaZ mutant was prepared. BM07-ΔphaZ (pBBR-phaZ) almost completely restored the original phenotype in terms of PHA composition. The level of 3HD and 3HDD in the complement strain was similar to those in the wild-type except the significantly lowered level of 3-hydroxydodecenoate (3HDDe). However, this difference could not be ascribable to a polar effect because the mutation of phaC2 in BM07 was not found to affect the monomer composition of PHA significantly compared with the wild-type. The lowered level of 3-hydroxydodecenoate (3HDDe) may be ascribable to the different expression level of PhaZ in wild-type and BM07-ΔphaZ (pBBR-phaZ).

Quantitative Characterization of Aromatic Monomer-Units in PHA from 11-POU

According to FIG. 2, gas chromatogram of methyl esters of the PHA produced in P. fluorescens BM07-ΔphaZ grown on a mixture of 50 mM fructose, 8 mM 11-phenoxyundecanoic acid and 1 mM salicylic acid revealed four major peaks at 17.9, 22.7, 26.6 and 30.1 min of retention time. The first three early appearing peaks were identified as the methyl ester of 3-hydroxy-5-phenoxyvalerate (5POHV), 3-hydroxy-7-phenoxyheptanoate (7POHH) and 3-hydroxy-9-phenoxynonanoate (9POHN), respectively from a standard mixture of the three methyl esters. Assuming a homologous series compounds, two mass spectra associated with the two GC peaks at 26.6 and 30.1 min were compared to find common fragmentation species. It was certain that the peak at 94 m/z was caused by phenol cation species Ph-OH$^+$. The peaks at 280.1 m/z (B) and 308.2 m/z (C) could be assigned to the molecular ion (M+) species for methyl-3-hydroxy-9-phenoxynonanoate and methyl-3-hydroxy-11-phenoxyundecanoate, respectively. The peaks at 262.1 m/z (B) and 290.2 m/z (C) could be assigned to water molecule minus ion (M-H$_2$O)$^+$ peaks from the molecular ion species. In (B), a series of peaks at 137.1, 206.1 and 248.1 m/z could be assigned to be sequentially induced through continuous deletion of one ethylene unit from the (M-H$_2$O)$^+$ peak at 262.1 m/z, and in (C), a series of peaks at 165.1, 234.1 and 276.1 m/z may be assigned to be induced through continuous deletion of one ethylene unit from the (M-H$_2$O)$^+$ peak at 290.2 m/z. Thus, based on the closely related mass fragmentation pattern between the two GC peaks of (B) and (C), the GC peak appeared at 30.1 min was identified as the methyl ester compound of 3-hydroxy-11-phenoxyundecanoate (11POHUN).

Figure 3A:
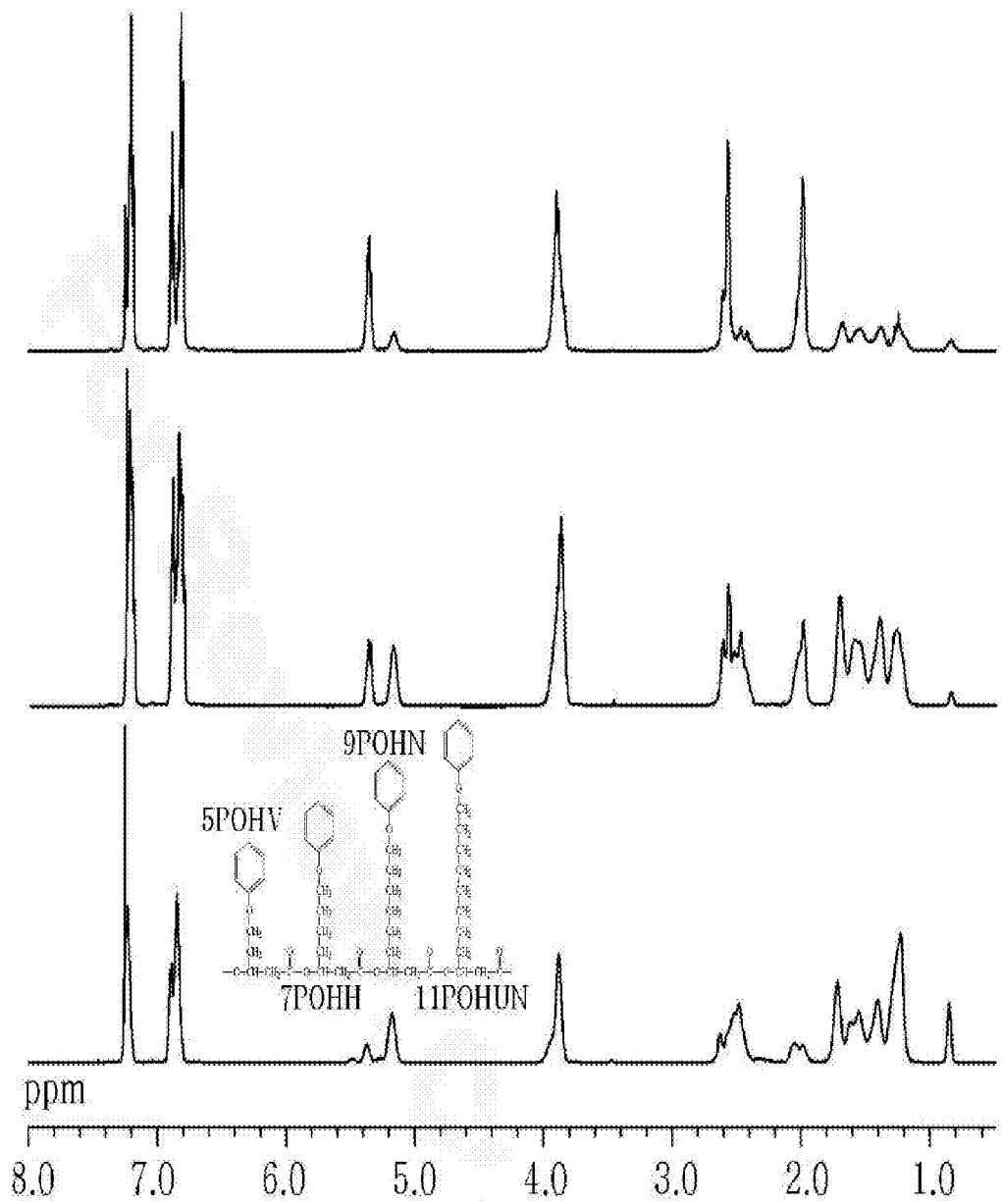

Quantitative analysis of the four monomer-units in the PHA from 11-POU was necessary to determine their exact ratio. Therefore, a detailed NMR analysis was performed to obtain well resolved signals associated with monomer constituents for quantitation. Among samples analyzed by NMR, sample 1 was prepared by culturing cells in a medium containing 50 mM fructose and 5 mM 11-POU at 30° C. and 175 rpm for 62 hours, sample 2 was prepared by culturing cells in a medium containing 50 mM fructose, 8 mM 11-POU and 1 mM salicylic acid at 30° C. and 175 rpm for 84 hours, sample 3 was prepared by culturing cell in a medium containing 50 mM fructose, 8 mM 11-POU and 1 mM salicylic acid at 30° C. and 175 rpm for 72 hours, and sample 4 was prepared by culturing cell in a medium containing 50 mM fructose, 8 mM 11-POU and 1 mM salicylic acid at 30° C. and 175 rpm for 62 hours. The upper spectrum in FIG. 3A were obtained by analyzing the PHAs having different ratios of monomer-units using a 500 MHz $^1$H-NMR spectrometer. Detailed chemical-shift assignments for the carbons and protons of the PHA having shorter three monomer-units were published previously. Among the proton peaks, the peaks at 5.36, 2.00 and 1.73 ppm were assigned to the protons originated from —O—CH(R)— (back-bone methine of 5POHV), —O—CH (CH$_2$—CH2-O-Ph)-(C=O)— (side-chain methylene adjacent to the back-bone methine in 5POHV) and —CH$_2$—CH2-O-Ph in 7POHH, which was identified in the analyses of $^1$H-$^1$H Homo COSY, $^1$H-$^{13}$C Hetero COSY, HMBC and DEPT spectrum.

Figure 3B:
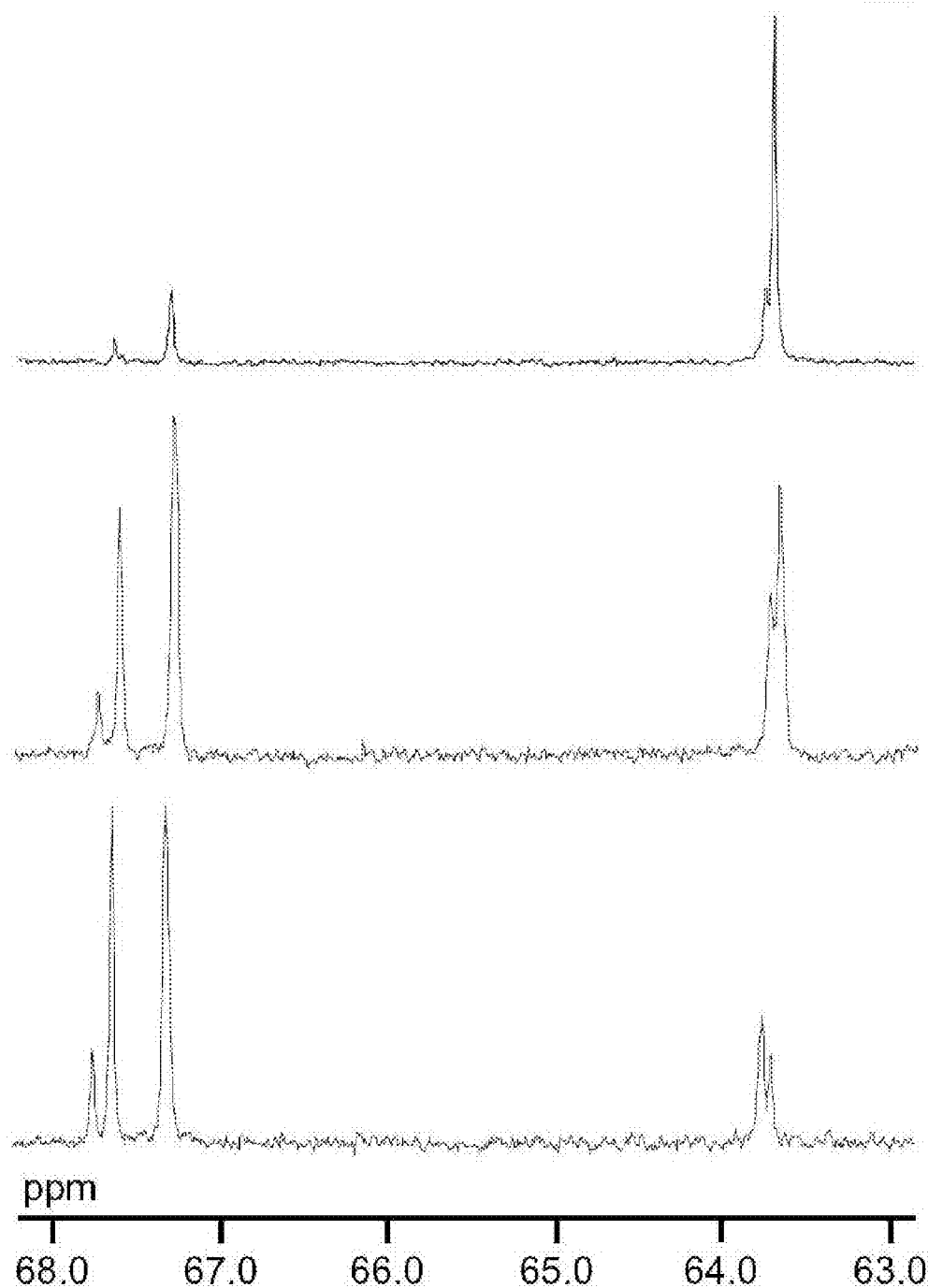
Figure 3C:
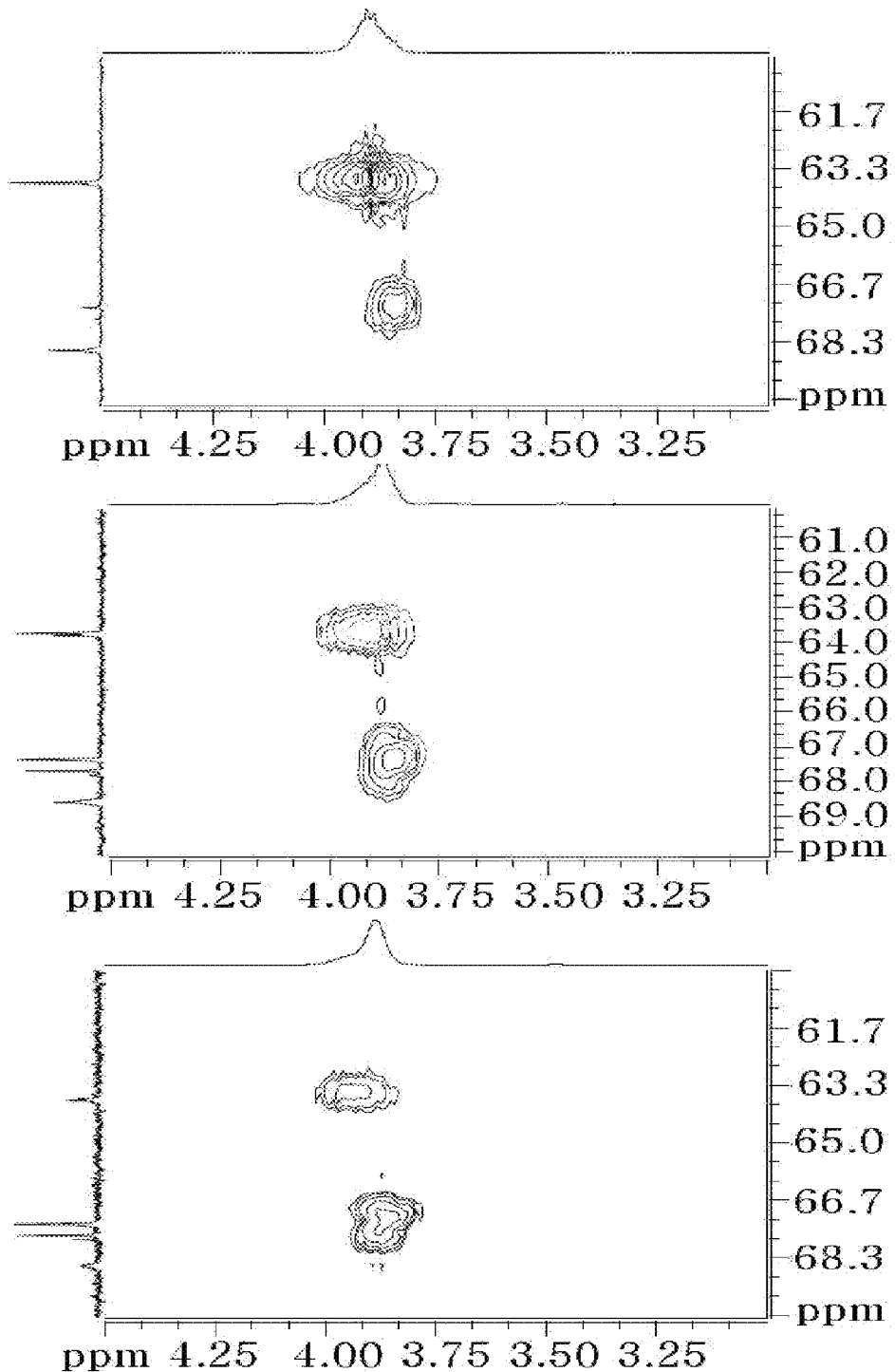

Since four monomer-units were detected in PHA, the ratio of the monomer-units was not calculable from proton NMR spectrum alone. In a previous study, the inventors suggested that any well resolved $^{13}$C signals for the similar type of chemical groups could be utilized for quantitative determination of the monomer-units. As shown in FIG. 3B, among the carbons analyzed, the expanded spectral region for the methylene carbon in —CH$_2$—O-Ph exhibited well separated absorptions at 63.7, 67.35, 67.67 and 67.80 ppm enough to be integrated accurately for quantitation, in which the four absorption peaks are ascribable to the carbons in 5POHV, 7POHH, 9POHN and 11POHUN. As shown in FIG. 3C, in the 2-D Hetero-COSY spectrum, two cross-peaks occurred, the upper one associated with 5POHV and the lower one with the other longer three monomer-units. An increase in the level of longer monomer-units than 5POHV caused to intensify the lower cross-peak as well as shift of the maximum absorption of the methylene proton attached to phenoxy group (—CH$_2$—O-Ph) from 3.92 to 3.89 ppm. Actually, the protons in —CH$_2$—O-Ph for all four monomer-units were not resolved and exhibited a single proton peak. However, the absorptions in back-bone methine proton —O—CH(R)— are grouped into two groups, 5.36 ppm assignable to 5POHV and 5.17 ppm to a group of 7POHH, 9POHN and 11POHUN.

TABLE 2

Comparison of mol % calculated from the integrated area ratio for the back-bone methane proton (two signals, the, down-field one associated with 5POHV and the other up-field one with 7POHH, 9POHN and 11POHUN) and phenoxy-group adjoining methylene carbon (four signals associated with the four monomer-units, respectively).

| Sample | Strain used in PHA synthesis | Carbon source$^a$ | Inhibitor$^a$ | Culture time (h) | Chemical group used in calculation | 5POHV$^b$ (mol %) | 7POHH (mol %) | 9POHN (mol %) | 11POHUN (mol %) |
|---|---|---|---|---|---|---|---|---|---|
| Sample 1 | BM07-ΔphaG$^c$ | 50 mM fructose 5 mM 11-POU | None | 62 | C$^{13}$ NMR Phenoxy-CH$_2$— | 81 | 15 | 4 | |
| | | | | | H NMR —O—CH(R)— | 82 | [18]$^e$ | | |
| Sample 2 | BM07-ΔphaG | 50 mM fructose 8 mM 11-POU | 1 mM SA | 84 | C$^{13}$ NMR Phenoxy-CH$_2$— | 41 | 35 | 19 | 5 |
| | | | | | H NMR —O—CH(R)— | 44 | [56] | | |

TABLE 2-continued

Comparison of mol % calculated from the integrated area ratio for the back-bone methane proton (two signals, the, down-field one associated with 5POHV and the other up-field one with 7POHH, 9POHN and 11POHUN) and phenoxy-group adjoining methylene carbon (four signals associated with the four monomer-units, respectively).

| Sample | Strain used in PHA synthesis | Carbon source[a] | Inhibitor[a] | Culture time (h) | Chemical group used in calculation | 5POHV[b] (mol %) | 7POHH (mol %) | 9POHN (mol %) | 11POHUN (mol %) |
|---|---|---|---|---|---|---|---|---|---|
| Sample 3 | BM07-ΔphaG | 50 mM fructose 8 mM 11-POU | 1 mM SA | 72 | $C^{13}$ NMR Phenoxy-$CH_2$— | 29 | 40 | 25 | 6 |
|  |  |  |  |  | H NMR —O—CH(R)— | 32 | [68] |  |  |
| Sample 4 | BM07-ΔphaZ | 50 mM fructose 8 mM 11-POU | 1 mM SA | 62 | $C^{13}$ NMR Phenoxy-$CH_2$— | 22 | 43 | 27 | 8 |
|  |  |  |  |  | H NMR —O—CH(R)— | —[d] | [—[d]] |  |  |

To check whether the monomer-unit ratio calculated from the carbon signals in Table 2 had validity for the quantitation of monomer-units, the sum of three contributions 7POHH, 1POHN and 11 POHUN was compared with the ratio calculated from the absorptions at 5.36 and 5.17 ppm. In the comparison, the PHA synthesized in BM07-ΔphaZ mutant (Sample 4) was excluded because the absorptions due to the presence of aliphatic monomer-units (~10% or less) caused an incorrect determination of the areas of the absorptions at 5.36 and 5.17 ppm associated with only aromatic monomer-units.

Thus, the ratio calculated from the carbon signals agreed well with that from the proton signals. In the present invention, the calculated monomer-unit ratios for the samples in Table 2 were used to obtain the standard curve for the determination of monomer-unit composition of aromatic PHA from 11-POU for use in the gas chromatographic characterization. In the previous study, a small amount of 11-POHUN was not identified and reported for the wild-type cells grown on 3 or 5 mM 11-POU/50 mM fructose. Because of its too small and broad peak on the GC chromatogram and similar retention time between the two methyl esters of 11-POHUN and 11-POU (28.5 and 28.9 min, respectively), the minor peak at 28.5 min was mistaken for the methyl ester of residual 11-POU at that time.

Delayed Accumulation of PHA from 11-POU in BM07 Strains by Salicylic Acid

Figure 4:
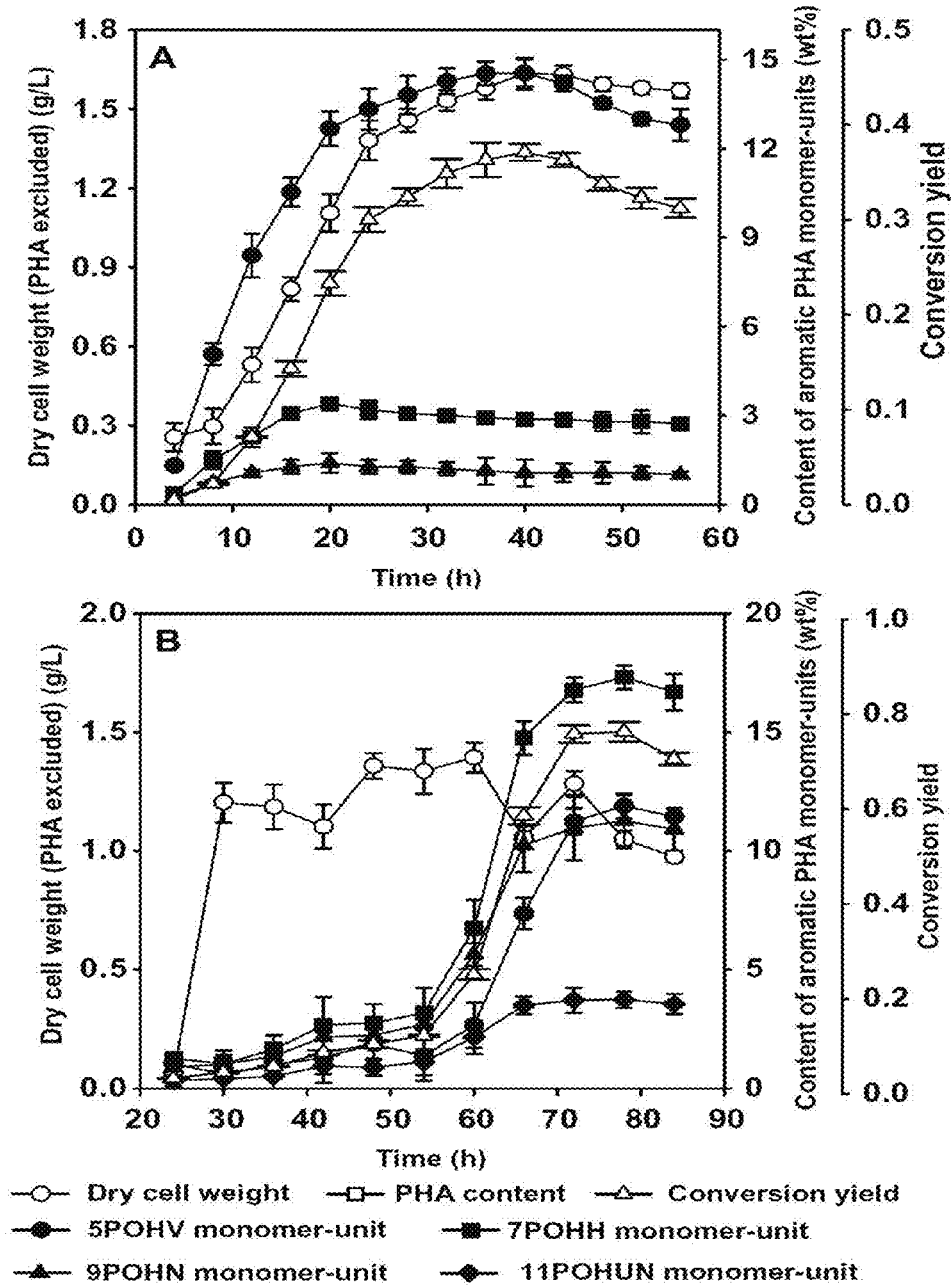
FIG. 4 shows the time-course profiles for cell growth, PHA content (aromatic monomer-unit only), and incorporation of the monomer-units derived from 11-POU. The cells were grown on a mixture of 50 mM fructose and 5 mM 11-POU in the absence (A and C) or presence (B and D) of 1 mM salicylic acid, in which (A) represents BM07 wild-type, (B) represents BM07-ΔphaZ mutant, and (C) and (D) represents BM07 (pBBR-phaZ). All values are averages in triplicate experiments.
Figure 4:
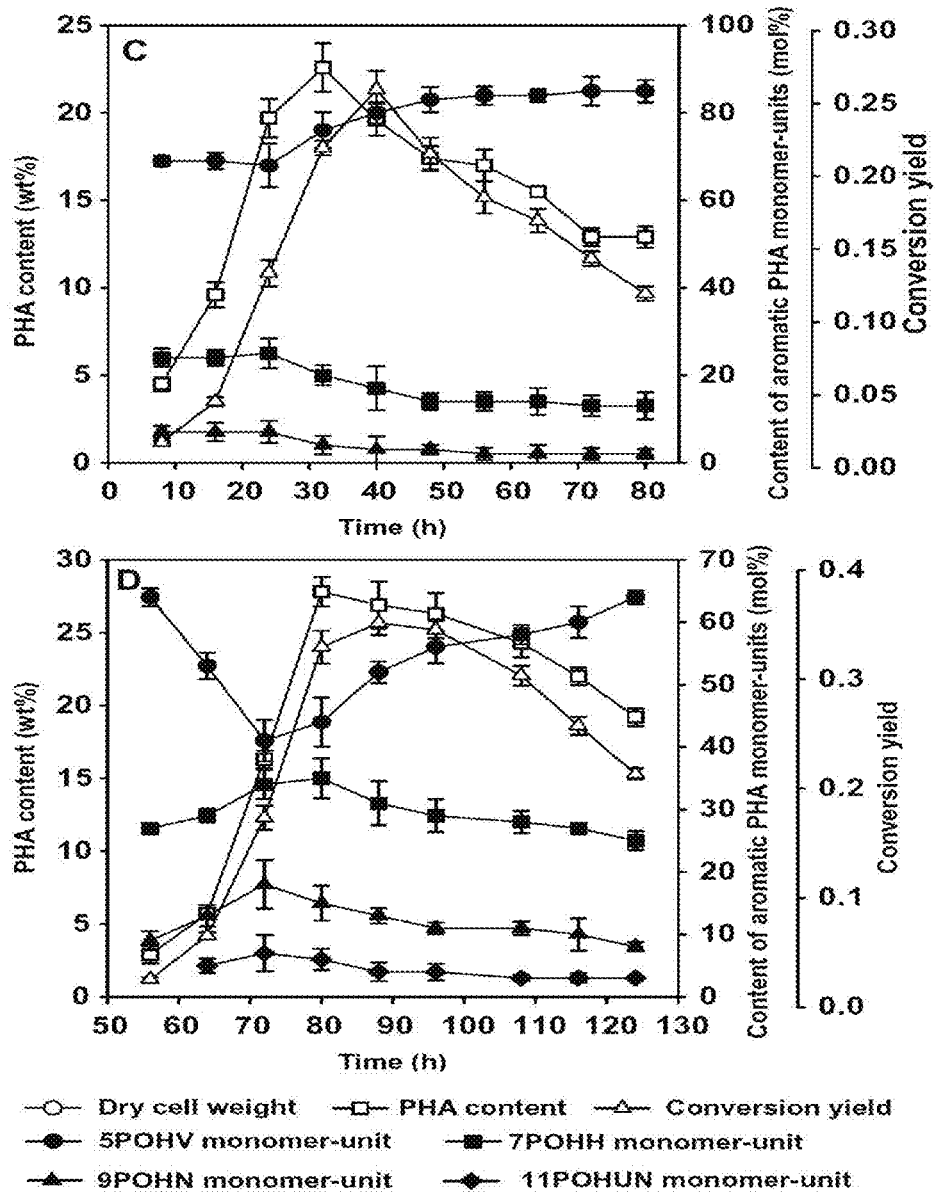

BM07 wild-type grown with a mixture of 50 mM fructose and 5 mM 11-POU accumulated aromatic PHA from 11-POU with fructose being utilized mainly for cell growth (less than 4 wt % aliphatic monomer-units was detected). As shown in FIG. 4, the cell growth and PHA accumulation occurred simultaneously in the absence of salicylic acid inhibitor. Both carbon sources were consumed within 30-40 hours. A similar growth-associated PHA accumulation was observed in BM07-Δ-phaZ mutant. When BM07-ΔphaZ was grown on the mixture of 50 mM fructose and 5 mM 11-POU with the presence of 1 mM salicylic acid, maximum cell growth occurred at 50-60 hours of cultivation but PHA accumulation was significantly delayed showing a maximum at around 70 hours of cultivation. Thus, as shown in FIG. 4, salicylic acid did not significantly delay the cell growth while it significantly retarded the accumulation of aromatic PHA from 11-POU. The delayed PHA accumulation can be ascribable to the inhibition of β-ketothiolase by salicyl-CoA. Since salicylic acid is not metabolized by P. fluorescens BM07, the delayed accumulation could not be considered to result from any change in its "effective" inhibitor concentration.

According to the mol % profile of aromatic monomer-units, recalculated from the data in FIG. 4, during the active PHA accumulation period between 60 and 70 hours, an increase in mol % of 5POHV (from 20 to 30) and a decrease in 9POHN level (from 29 to 21) were observed in BM07-ΔphaZ grown in the presence of salicylic acid, whereas the mol % of 7POHH and 11 POHUN remained constant. However, no significant change in the mole ratio of three monomer-units (5POHV, 7POHH and 9POHN) occurred in the wild-type grown in the absence of salicylic acid throughout the cultivation. Therefore, the change in monomer-unit ratio for salicylic acid treated cells is believed to be caused by the inhibitory effect of salicylic acid.

Modulation of Comonomer-Units by Salicylic Acid in BM07-ΔphaZ Grown in 11-POU

In the cometabolism of 1'-POU with 50 mM fructose in the wild-type, 5 mM of 11-POU was able to suppress the incorporation of aliphatic monomer-units down to less than ~20% of the total PHA content. Therefore, in the present invention, the concentration of coadded 11-POU was finally fixed at 5 mM (see Table 3) to minimize the incorporation of aliphatic monomers. Compared to the wild-type control grown in the absence of salicylic acid, an addition of 1 mM salicylic acid suppressed their incorporation further down to ~10% of the total PHA content and slightly increased the total PHA content. The content of aliphatic MCL-monomer-units in BM07-ΔphaZ grown in the absence of salicylic acid was drastically enhanced up to more than 50% of the total PHA. However, according to Table 3, an addition of 1 mM salicylic acid to the culture medium drastically reduced the level to ~10% of the total PHA comparable to the level of wild-type control but instead increased the content of aromatic PHA twice more than that in the absence of salicylic acid. Thus, the suppression effect of salicylic acid appeared to be much stronger in BM07-ΔphaZ than the wild-type. This implies that, in addition to its inhibitory effect on the β-oxidation, salicylic acid can also inhibit the accumulation of aliphatic MCL-PHA in BM07 strains grown on the mixed carbon source of which the aliphatic monomer precursors are derived via PhaG from fructose. Similarly as reported for the wild-type and BM07-ΔphaG mutant, in BM07-ΔphaZ, salicylic acid also induced a shifting of the distribution of aromatic monomer-units to longer units. According to Table 3, BM07-ΔphaZ mutant exhibited a very high yield of conversion of 11-POU to PHA up to about 70-80%. The longest monomer-unit 11-POHUN, not reported in literature yet, which has the same number of carbon as the substrate molecule 11-POU, was more effectively incorporated in BM07-ΔphaZ.

TABLE 3

Effect of salicylic acid on the monomer compositions of polyesters produced in *P. fluorescens* BM07 strains grown on a mixture of 50 mM fructose and 5 mM 11-POU under one-step cultivation condition (30° C.)

| BM07 strain | Co-added compounds (mM) | Culture time (h) | Dry cell weight (g/L) | Polyester content (wt. %)[a] | PHA (aliphatic monomer) (wt. %) | PHA (aromatic monomer) (wt. %) |
|---|---|---|---|---|---|---|
| Wild-type | No inhibitor | 48 | 1.74 ± 0.11 | 22.4 ± 2.3 | 4.5 ± 0.3 | 17.9 ± 2.0 |
| | No inhibitor | 72 | 1.64 ± 0.13 | 22.9 ± 1.7 | 3.2 ± 0.5 | 19.7 ± 1.2 |
| | 1 mM Salicylic acid | 48 | 1.36 ± 0.10 | 23.9 ± 1.1 | 3.1 ± 0.2 | 20.8 ± 0.9 |
| | 1 mM Salicylic acid | 72 | 1.78 ± 0.06 | 29.3 ± 2.1 | 2.5 ± 0.5 | 26.8 ± 1.6 |
| BM07-ΔphaZ | No inhibitor | 72 | 1.82 ± 0.08 | 44.5 ± 2.3 | 23.7 ± 0.9 | 20.8 ± 1.4 |
| | No inhibitor | 96 | 1.82 ± 0.15 | 44.7 ± 3.6 | 23.1 ± 0.8 | 21.6 ± 2.8 |
| | 1 mM Salicylic acid | 72 | 1.68 ± 0.11 | 48.9 ± 1.9 | 4.8 ± 0.3 | 44.1 ± 1.6 |
| | 1 mM Salicylic acid | 96 | 1.72 ± 0.09 | 53.0 ± 1.8 | 4.3 ± 0.4 | 48.7 ± 1.4 |

| BM07 strain | Co-added compounds (mM) | Monomer-unit composition (mol %)[b] | | | | Conversion yield[c] |
|---|---|---|---|---|---|---|
| | | 5POHV | 7POHH | 9POHN | 11-POHUN | |
| Wild-type | No inhibitor | 81.8 ± 0.7 | 14.9 ± 0.4 | 3.3 ± 0.3 | —[d] | 0.309 ± 0.007 |
| | No inhibitor | 80.9 ± 0.8 | 16.0 ± 0.5 | 3.1 ± 0.3 | — | 0.331 ± 0.005 |
| | 1 mM Salicylic acid | 30.3 ± 1.5 | 45.8 ± 0.4 | 19.0 ± 1.0 | 4.9 ± 0.1 | 0.260 ± 0.012 |
| | 1 mM Salicylic acid | 46.6 ± 0.6 | 35.1 ± 0.3 | 16.2 ± 1.0 | 2.1 ± 0.1 | 0.451 ± 0.013 |
| BM07-ΔphaZ | No inhibitor | 80.0 ± 1.1 | 16.3 ± 0.7 | 3.7 ± 0.4 | — | 0.381 ± 0.008 |
| | No inhibitor | 80.2 ± 1.1 | 15.8 ± 0.8 | 4.0 ± 0.3 | — | 0.401 ± 0.004 |
| | 1 mM Salicylic acid | 28.1 ± 1.5 | 39.8 ± 0.5 | 25.3 ± 0.9 | 6.8 ± 0.1 | 0.670 ± 0.017 |
| | 1 mM Salicylic acid | 25.7 ± 0.6 | 41.0 ± 0.5 | 24.9 ± 1.2 | 8.4 ± 0.1 | 0.751 ± 0.007 |

To assess how PhaZ affects the comonomer composition of aromatic PHA, the PhaZ over-expressed strain BM07 (pBBR-phaZ) was also grown on 50 mM fructose/5 mM 11-POU in the absence (FIG. 3C) or presence (FIG. 3D) of 1 mM salicylic acid. The overexpression of PhaZ suppressed the incorporation of aliphatic monomer-units down to less than 8% of the total PHA content at the maximum accumulation for non-salicylic acid cells and 4% for salicylic acid treated cells, twice more than in the wild-type cells. In contrast, the content of aromatic PHA at the maximum value in C and D of FIG. 4 was not affected by the PhaZ overexpression when compared to the content in the wild-type cells in Table 3. This may indicate that the PhaZ depolymerase degraded aliphatic monomer-units more preferentially than aromatic monomer-units even during PHA synthesis. The maximum yield of conversion of 11-POU to PHA for the BM07 (pBBR-phaZ) cells was 0.26 and 0.34 for non-salicylic acid cells and salicylic acid treated cells, which were comparable to that (0.37) for the wild-type cells but significantly lower than that (0.75) for BM07-ΔphaZ mutant.

For salicylic acid treated BM07(pBBR-phaZ), a decrease in the level of 5POHV and an increase in the level of 7POHH, 9POHN and 11POHUN were noticed at the initial PHA accumulation stage, followed by the reversed change in their contents after the maximum PHA accumulation. It is likely that after the maximum PHA accumulation, PHA degradation occurred faster than PHA synthesis. Meanwhile the hydrolyzed longer monomers are shortened via β-oxidation and thus the shortened monomer-units are reincorporated to produce shorter side-chain PHA under such dynamic condition of polymerization and depolymerization. It is thus evident that the PhaZ depolymerase plays a secondary role in the production of shorter monomer-unit precursors. Therefore, the blocking of PHA degradation may be a means to enhance the production of longer side-chain aromatic PHA.

Enhancement of the Conversion Yield of Other ω-Aromatic Group Fatty Acid by Salicylic Acid In the production of functional PHA from expensive substrates, the yield of conversion of the substrates to the PHA is an important parameter for economic reason. In the previous study of the inventors, the conversion yield of 5-phenylvalerate (5PV) for the production of poly(3-hydroxy-5-phenylvalerate) (P(3HPV)) was reported to be 0.33 in *P. putida* BM01 grown with 20 mM 5-phenylvalerate/50 mM butyric acid (see Table 4).

Effect of salicylic acid on the conversion yield of aromatic polyesters produced in *P. fluorescens* BM07 strains grown on a mixture of 50 mM fructose and 10 mM 5-PV or 6PC under one-step cultivation condition at 30° C.

| Aromatic substrate | Bacterial strain | Co-added compounds (mM) | Culture time (h) | Dry cell weight (g/L) | Aromatic PHA content (wt. %)[a] | Conversion yield[b] |
|---|---|---|---|---|---|---|
| 5PV | *P. putida* BM01 | [c] | 40 | 2.49 ± 0.13 | 46.3 ± 2.1 | 0.332 ± 0.003 |
| | BM07 wild-type | No inhibitor | 60 | 2.02 ± 0.15 | 31.1 ± 2.0 | 0.360 ± 0.007 |
| | | 1 mM Salicylic acid | 72 | 1.98 ± 0.08 | 34.2 ± 1.5 | 0.378 ± 0.011 |
| | BM07-ΔphaZ | No inhibitor | 60 | 2.04 ± 0.11 | 33.2 ± 0.8 | 0.388 ± 0.005 |
| | | 1 mM Salicylic acid | 72 | 2.10 ± 0.06 | 49.9 ± 1.3 | 0.591 ± 0.002 |
| 6PC | *P. putida* BM01 | [d] | 40 | 1.45 ± 0.07 | 29.7 ± 2.3 | 0.221 ± 0.004 |
| | BM07 wild-type | No inhibitor | 48 | 1.86 ± 0.13 | 17.2 ± 1.3 | 0.160 ± 0.001 |
| | | 1 mM Salicylic acid | 60 | 1.78 ± 0.13 | 32.8 ± 1.7 | 0.312 ± 0.003 |

Effect of salicylic acid on the conversion yield of aromatic polyesters produced in *P. fluorescens* BM07 strains grown on a mixture of 50 mM fructose and 10 mM 5-PV or 6PC under one-step cultivation condition at 30° C.

| Aromatic substrate | Bacterial strain | Co-added compounds (mM) | Culture time (h) | Dry cell weight (g/L) | Aromatic PHA content (wt. %)[a] | Conversion yield[b] |
|---|---|---|---|---|---|---|
| | BM07-ΔphaZ | No inhibitor | 60 | 1.66 ± 0.10 | 22.2 ± 0.9 | 0.192 ± 0.005 |
| | | 1 mM Salicylic acid | 72 | 1.72 ± 0.08 | 35.1 ± 1.2 | 0.333 ± 0.002 |

When grown on a mixture of 10 mM 6-phenylcaproate (6PC) and 30 mM butyric acid, BM01 accumulated P(5 mol % 3-hydroxy-4-phenylbutyrate-co-95 mol % 3-hydroxy-6-phenylcaproate) with a conversion yield of 0.22. When BM07 wild-type and mutant strains were cultivated on a mixture of 50 mM fructose and 10 mM 5PV or 6PC, similar to the case of 11-POU, an addition of 1 mM salicylic acid improved the conversion yield of the two phenyl substituted fatty acids more efficiently than in BM01 cells reported earlier. A higher yield enhancement in BM07-ΔphaZ mutant was observed for 5PV substrate, which was increased up to 0.59. Thus, the effect of phaZ deletion on the conversion yield was more effective against odd number of carbon substrate than even number of carbon substrate. In addition, BM07 strains accumulated P(3-hydroxy-6-phenylcaproate)(P(3HPC)) homopolymer in contrast with *P. putida* BM01. The cultivation of BM07 strains on the mixed substrate of 50 mM fructose and 10 mM 5PV or 6PC produced aromatic PHA free from aliphatic components in the absence and presence of salicylic acid. Thus BM07 strains are considered to be better aromatic PHA producers than BM01 strain even though the latter accumulates more amounts of PHA during shorter cultivation time.

Effect of Side-Chain Length on the Thermal Transition of MCL-PHA

Figure 5:
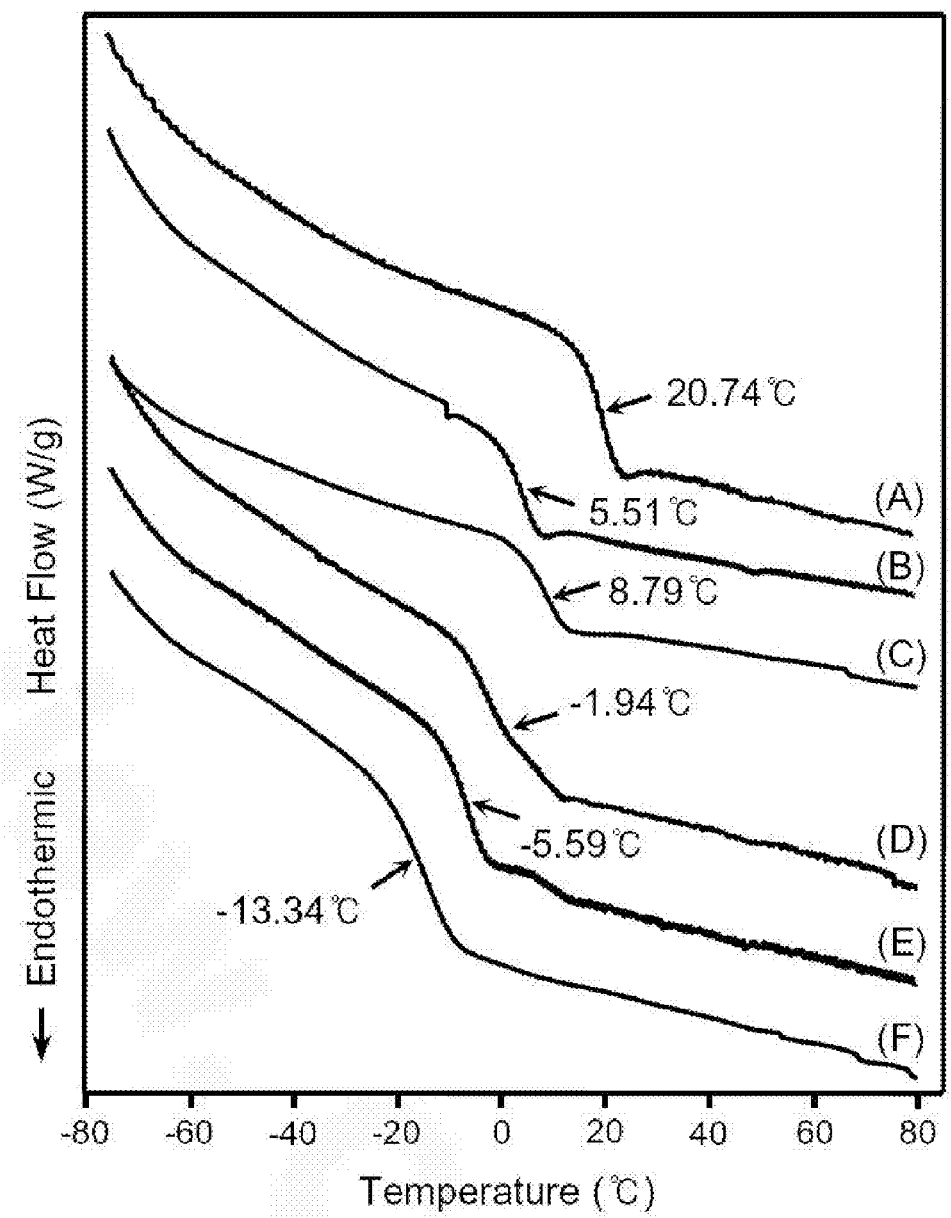
FIG. 5 shows the effects of side-chain length on the glass transition of PHA produced in BM07 wild-type and mutants, in which (A) represents P(3HPV) homopolymer, (B) represents P(3HPC) homopolymer, (C) represents P(81 mol % 5POHV-co-15 mol % 7POHH-co-4 mol % 9POHN), (D) represents P(41 mol % 5POHV-co-35 mol % 7POHH-co-19 mol % 9POHN-co-5 mol % 11POHUN), (E) represents P(29 mol % 5POHV-co-40 mol % 7POHH-co-25 mol % 9POHN-co-6 mol % 11 POHUN), and (F) represents P(22 mol % 5POHV-co-43 mol % 7POHH-co-27 mol % 9POHN-co-8 mol % 11 POHUN).

As shown in FIG. 5, in contrast with aliphatic MCL-PHA, aromatic MCL-PHA did not exhibit any melt transition, instead glass transition occurred for all types of samples. In the present invention, the amorphous nature of the aromatic PHA was supported by wide-angle X-ray diffraction analysis.

The two short side-chain homopolymers P(3HPV) and P(3HPC) had a glass transition at 21 and 6° C., respectively. The side-chain lengthening of P(3HPC) in comparison with P(3HPV) is believed to lower Tg. A similar Tg lowering was also observed in the aromatic PHA with a wide distribution of different side-chain lengths synthesized from 11-POU. In the mixed copolymer system, the Tg lowering is clearly due to a side-chain lengthening effect. The four samples (C), (D), (E) and (F) in FIG. 5 are the same samples of which the monomer composition was analyzed in Table 2 using the $^{13}$C-NMR peak ratios. It is interesting to note the transparency of long room-temperature annealed P(3HPV) polymer film (~3 mm thick) whereas other MCL-PHA polymer films are generally translucent or opaque.

As described above, according to the present invention, when the gene of polyhydroxyalkanoic acid depolymerase is deleted from *Pseudomonas fluorescens* BM07 and the salicylic acid is added during cultivation of cells, the length of an aromatic spacer in functional group-substituted MCL-PHA can be effectively increased, and the conversion yield of 11-POU to PHA in *Pseudomonas fluorescens* BM07 can be significantly increased, thereby yielding a significantly larger amount of high-purity long-chain aromatic polyhydroxyalkanoic acid than in the wild-type.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method for producing a polyhydroxyalkanoic acid (PHA) containing aromatic monomer-units, the method comprising:
   growing a phaZ gene-deleted mutant *Pseudomonas fluorescens* in a medium containing a sugar, a substituted aromatic carboxylic acid, and a salicylic acid to yield a high-purity aromatic polyhydroxyalkanoic acid containing a high content of aromatic monomer-units.

2. The method of claim 1, wherein the sugar is fructose.

3. The method of claim 1, wherein the content of the sugar in the medium is 50 to 70 mM.

4. The method of claim 1, wherein the substituted aromatic carboxylic acid is substituted with a phenyl, a substituted phenyl or a phenoxy group.

5. The method of claim 1, wherein the substituted aromatic carboxylic acid is 11-phenoxyundecanoic acid (11-POU).

6. The method of claim 1, wherein the content of the substituted aromatic carboxylic acid is 3 to 10 mM.

7. The method of claim 1, wherein the content of the salicylic acid in the medium is 0.1 to 2 mM.

8. The method of claim 1, wherein the *Pseudomonas fluorescens* is *Pseudomonas fluorescens* BM07 (Accession no.: KCTC 10005BP).

9. The method of claim 1, wherein the medium is M1 mineral salts medium (1.06 g (NH4)2SO4, 2.3 g KH2PO4, 7.3 g Na2HPO4.12H2O, 0.25 g MgSO4.7H2O, 0.3 g NaHCO3, 0.1 g CaCl2.2H2O, 0.03 g ferric ammonium citrate, and 2 ml microelement solution).

10. The method of claim 1, wherein the aromatic monomer unit is selected from the group consisting of 3-hydroxy-5-phenoxyvalerate (5POHV), 3-hydroxy-7-phenoxyheptanoate (7POHH), 3-hydroxy-9-phenoxynonanoate (9POHN), and 3-hydroxy-11-phenoxyundecanoate (11POHUN).

* * * * *